(12) United States Patent
Xerogeanes et al.

(10) Patent No.: US 11,517,414 B2
(45) Date of Patent: Dec. 6, 2022

(54) GRAFT PREPARATION SYSTEM

(71) Applicant: Arthrex, Inc., Naples, FL (US)

(72) Inventors: John Xerogeanes, Atlanta, GA (US); Jeffrey Jackson, Salt Lake City, UT (US); Jacob Jolly, Naples, FL (US); Justin Boyle, Naples, FL (US); Zachary Ingwer, Naples, FL (US); Lai Saeteurn, Naples, FL (US)

(73) Assignee: Arthrex, Inc., Naples, FL (US)

( * ) Notice: Subject to any disclaimer, the term of this patent is extended or adjusted under 35 U.S.C. 154(b) by 626 days.

(21) Appl. No.: 16/654,601

(22) Filed: Oct. 16, 2019

(65) Prior Publication Data

US 2021/0113319 A1  Apr. 22, 2021

(51) Int. Cl.
| | |
|---|---|
| *A61B 17/04* | (2006.01) |
| *A61F 2/00* | (2006.01) |
| *A61B 17/06* | (2006.01) |
| *A61F 2/08* | (2006.01) |
| *A61B 17/28* | (2006.01) |

(52) U.S. Cl.
CPC ........ *A61F 2/0095* (2013.01); *A61B 17/0483* (2013.01); *A61B 17/06133* (2013.01); *A61F 2/0811* (2013.01); *A61B 17/282* (2013.01); *A61B 2017/0404* (2013.01); *A61F 2220/0075* (2013.01); *A61F 2240/00* (2013.01)

(58) Field of Classification Search
CPC .......... A61B 17/0483; A61B 17/06133; A61B 17/282; A61B 2017/0404; A61F 2/0811; A61F 2220/0075; A61F 2240/00
See application file for complete search history.

(56) References Cited

U.S. PATENT DOCUMENTS

| | | | | |
|---|---|---|---|---|
| 2,618,268 A | | 11/1952 | English | |
| 3,627,120 A | * | 12/1971 | Bordeau | A61B 17/06133 206/408 |
| 4,700,833 A | * | 10/1987 | Smith | A61B 17/06138 229/87.5 |
| 5,092,455 A | * | 3/1992 | Leary | A61B 17/06133 206/483 |

(Continued)

FOREIGN PATENT DOCUMENTS

| | | |
|---|---|---|
| EP | 2777613 | 9/2014 |
| EP | 2923672 | 9/2015 |
| WO | 2017189096 | 11/2017 |

OTHER PUBLICATIONS

CONMED, Concept GraFix, Website, 2019.

(Continued)

*Primary Examiner* — Ryan J. Severson
(74) *Attorney, Agent, or Firm* — Carlson, Gaskey & Olds, P.C.

(57) ABSTRACT

A graft preparation system includes a fixation implant including a strand of suture wrapped around a graft preparation card. A tenaculum includes a first arm having a first tooth and a second arm having a second tooth that are pivotally connected at a pivot. The first arm includes a slot between the first tooth and the pivot that receives the graft preparation card. A tape suture assembly includes a tape suture and a first suture strand. The tape suture is positioned on a graft, and the tape suture is attached to the graft with a stitch formed with the first suture strand.

20 Claims, 12 Drawing Sheets

(56) References Cited

U.S. PATENT DOCUMENTS

| | | | |
|---|---|---|---|
| 5,121,836 A * | 6/1992 | Brown | A61B 17/06138 |
| | | | 206/63.3 |
| 5,169,041 A | 12/1992 | Tan | |
| 5,425,445 A * | 6/1995 | Brown | A61B 17/06138 |
| | | | 206/380 |
| 5,683,400 A | 11/1997 | McGuire | |
| 6,080,184 A * | 6/2000 | Peters | A61B 17/06133 |
| | | | 606/228 |
| 6,260,696 B1 * | 7/2001 | Braginsky | A61B 17/06133 |
| | | | 206/380 |
| 7,611,008 B2 * | 11/2009 | Ruffieux | A61B 50/30 |
| | | | 206/339 |
| 7,708,747 B2 | 5/2010 | Bjerken | |
| 8,029,563 B2 | 10/2011 | House et al. | |
| 8,298,289 B2 | 10/2012 | White et al. | |
| 8,357,203 B2 | 1/2013 | White et al. | |
| 8,403,947 B2 | 3/2013 | Ochiai | |
| 9,060,768 B2 | 6/2015 | Ferragamo et al. | |
| 9,101,461 B2 | 8/2015 | Albertorio et al. | |
| 9,192,375 B2 | 11/2015 | Skinlo et al. | |
| 9,357,991 B2 | 6/2016 | Denham et al. | |
| 9,387,065 B2 * | 7/2016 | Marks | A61B 17/0483 |
| 9,439,752 B2 * | 9/2016 | Marks | A61B 17/06138 |
| 9,468,433 B2 | 10/2016 | Denham et al. | |
| 9,538,999 B2 * | 1/2017 | Spivey | A61B 17/0401 |
| 9,572,566 B2 | 2/2017 | Skinlo et al. | |
| 9,622,742 B2 | 4/2017 | Spenciner | |
| 9,993,332 B2 * | 6/2018 | Woodruff | A61F 2/0811 |
| 10,123,792 B2 | 11/2018 | Pilgeram | |
| 10,182,903 B2 | 1/2019 | Sengun | |
| 10,292,699 B2 * | 5/2019 | Spivey | A61B 17/0483 |
| 10,350,054 B2 * | 7/2019 | Marks | A61F 2/08 |
| 10,357,355 B2 | 7/2019 | Woodruff et al. | |
| 10,383,720 B2 | 8/2019 | Gustafson | |
| 10,729,535 B2 * | 8/2020 | Marks | A61F 2/08 |
| 10,779,932 B2 | 9/2020 | Spenciner | |
| 10,939,908 B2 * | 3/2021 | Oldham | A61B 17/06061 |
| 11,229,428 B2 | 1/2022 | Jackson | |
| 11,229,513 B2 | 1/2022 | Sengun | |
| 11,241,305 B2 | 2/2022 | Denham et al. | |
| 11,395,727 B2 | 7/2022 | Gustafson | |
| 2004/0254609 A1 | 12/2004 | Esplin | |
| 2007/0173887 A1 | 7/2007 | Sasaki | |
| 2007/0235359 A1 * | 10/2007 | Ruffieux | A61B 50/30 |
| | | | 206/339 |
| 2007/0250163 A1 | 10/2007 | Cassani | |
| 2013/0116730 A1 | 5/2013 | Denham et al. | |
| 2013/0274768 A1 | 10/2013 | Skinlo et al. | |
| 2015/0223927 A1 | 8/2015 | Ferragamo et al. | |
| 2016/0015389 A1 | 1/2016 | Belson | |
| 2017/0128063 A1 | 5/2017 | Jackson | |
| 2017/0172570 A1 * | 6/2017 | Wentling | B65D 5/4266 |
| 2017/0189162 A1 | 7/2017 | Spenciner | |
| 2018/0206841 A1 * | 7/2018 | Oldham | A61B 17/0401 |
| 2019/0038276 A1 | 2/2019 | Jackson | |
| 2020/0323623 A1 | 10/2020 | Marks et al. | |
| 2021/0007840 A1 | 1/2021 | Spenciner | |
| 2021/0113319 A1 * | 4/2021 | Xerogeanes | A61B 17/06133 |
| 2022/0125425 A1 | 4/2022 | Hall | |

OTHER PUBLICATIONS

The Extended European Search Report for European Patent Application No. 20202006.1 dated Mar. 19, 2021.

"QuadLink Grant Preparation with the FiberTag TightRope Implant", Arthrex, 2022.

\* cited by examiner

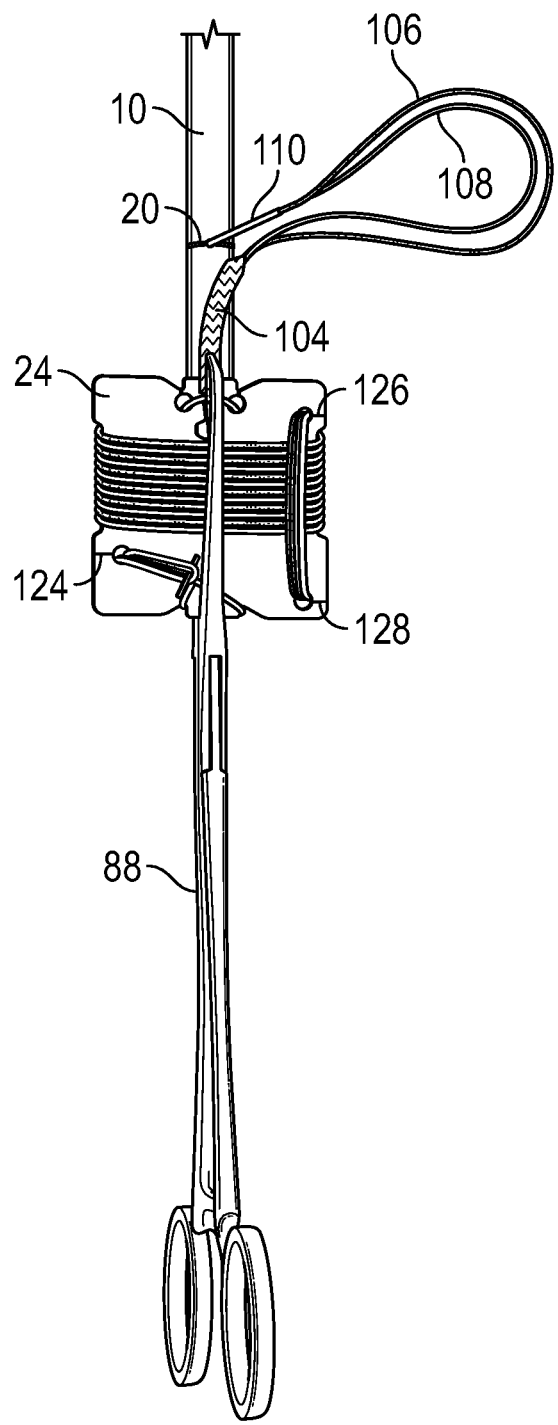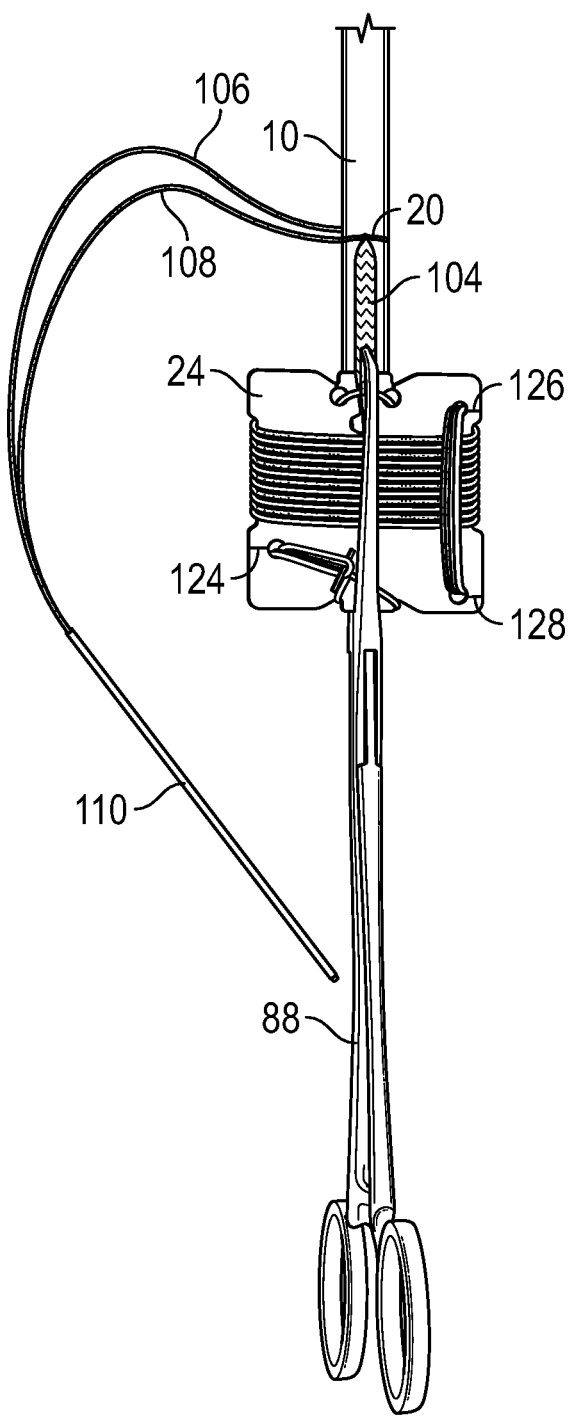
FIG. 9A
FIG. 9B

GRAFT PREPARATION SYSTEM

BACKGROUND

This disclosure relates to a graft preparation system.

SUMMARY

Grafts are prepared prior to surgery to provide reinforcement. Sutures can be sewn into the graft with a needle to provide a scaffold to provide additional strength.

A graft preparation system includes a fixation implant including two strands of suture and a suture construct. The suture construct includes a first adjustable eyesplice and a second adjustable eyesplice interconnected by a loop to form an adjustable loop. The graft preparation system includes a graft preparation card, and the two strands of suture of the fixation implant are wrapped around the graft preparation card. The first arm includes a slot that receives the graft preparation card. The graft preparation system includes a tenaculum including a first arm having a first tooth and a second arm having a second tooth. The first tooth of the tenaculum pierces a tape suture, and the second tooth of the tenaculum pierces the graft. The graft preparation system includes a tape suture assembly including the tape suture, a first suture strand, and a second suture strand. The tape suture is attached to the graft with stitches formed with the first suture strand and the second suture strand. The fixation implant is attached to the graft with a stitch formed with the first suture strand and the second suture strand that passes through the adjustable loop.

In one example, a graft preparation system includes a fixation implant including a button with a first button hole and a second button hole, a first strand of suture that passes through the first button hole, and a suture construct that passes through both the first button hole and the second button hole. The suture construct includes a first free strand and a second free strand, and the suture construct includes a first adjustable eyesplice and a second adjustable eyesplice interconnected by a loop to form an adjustable loop. The graft preparation system includes a graft preparation card substantially rectangular in shape and including a graft edge, an opposing tenaculum edge, a first cleat edge that defines a first cleat, and an opposing second cleat edge that defines a second cleat. The graft preparation card includes a passage having a longitudinal axis extending from the graft edge, a first hole and a second hole located on each side of the passage, a first slit that extends from the graft edge to the first hole, and a second slit that extends from the graft edge to the second hole. The graft preparation card includes a first groove on the graft edge located above the first hole, a second groove on the graft edge located above the second hole, a third groove located on the tenaculum edge, and a fourth groove is located on the tenaculum edge. A line extending between the first groove and the third groove is substantially parallel to the longitudinal axis and a line between the second groove and the fourth groove is substantially parallel to the longitudinal axis. The first strand of suture, the first free strand, and the second free strand of the fixation implant are wrapped around the graft preparation card. The first adjustable eyesplice of the suture construct is received in the first groove and the third groove of the graft preparation card, and the second adjustable eyesplice of the suture construct is received in the second groove and the fourth groove of the graft preparation card. The first adjustable eyesplice is slidable through the first slit to be received in the first hole, and the second adjustable eyesplice is slidable through the second slit to be received in the second hole. The loop of the suture construct is located between the first hole and the second hole. The graft preparation system includes a tenaculum including a first arm having a first tooth and a second arm having a second tooth. The first arm and the second arm are pivotally connected at a pivot, and the first tooth and the second tooth are at a distal end of the first arm and the second arm, respectively, of the tenaculum. The first arm between the first tooth and the pivot includes a slot that receives the graft preparation card. The graft preparation system includes a tape suture assembly including a tape suture, a first suture strand, a second suture strand, and a needle attached to the first suture strand and the second suture strand. The tape suture is positioned on a graft, the first suture strand and the second suture strand extend from a distal end portion of the tape suture, and the tape suture is attached to the graft with stitches formed by the first suture strand and the second suture strand. The first tooth of the tenaculum pierces a proximal end portion of the tape suture, the second tooth of the tenaculum pierces a proximal end portion of the graft, and the first suture strand and the two free strands of the suture construct wrap around a first cleat and a second cleat of the graft preparation card.

In another example, a graft preparation system includes a fixation implant including at least one strand of suture and a graft preparation card. The at least one strand of suture of the fixation implant is wrapped around the graft preparation card. The graft preparation system includes a tenaculum including a first arm having a first tooth and a second arm having a second tooth, and the first arm and the second arm are pivotally connected at a pivot. The first arm between the first tooth and the pivot includes a slot that receives the graft preparation card. The graft preparation system includes a tape suture assembly including a tape suture and a first suture strand. The tape suture is positioned on a graft, and the first suture strand extends from a distal end portion of the tape suture. The tape suture is attached to the graft with a stitch formed with the first suture strand, the first tooth of the tenaculum pierces a proximal end portion of the tape suture, and the second tooth of the tenaculum pierces a proximal end portion of the graft.

In another embodiment, the first tooth and the second tooth are at a distal end of the first arm and the second arm, respectively, of the tenaculum.

In another embodiment, the graft preparation card is substantially rectangular in shape and includes a graft edge, an opposing tenaculum edge, a first cleat edge, and an opposing second cleat edge. The graft preparation card includes a passage having a longitudinal axis extending from the graft edge.

In another embodiment, the graft preparation card includes a curved portion in communication with the passage, and the passage and the curved portion define a keyhole shaped opening.

In another embodiment, the graft preparation card includes a first hole and a second hole located on each side of the passage, a first slit extends from the graft edge to the first hole, and a second slit extends from the graft edge to the second hole.

In another embodiment, a first groove on the graft edge is located above the first hole, a second groove on the graft edge is located above the second hole, a third groove is located on the tenaculum edge, a fourth groove is located on the tenaculum edge. A line extending between the first groove and the third groove is substantially parallel to the longitudinal axis, and a line between the second groove and the fourth groove is substantially parallel to the longitudinal axis.

In another embodiment, the first cleat edge defines a first cleat, the opposing second cleat edge defines a second cleat, a third hole is located in an area where the tenaculum edge and the first cleat edge intersect, a fourth hole is located in an area where the tenaculum edge and the opposing second cleat edge intersect, and a fifth hole is located in an area where the graft edge and the opposing second cleat edge intersect. A line between the fourth hole and the fifth hole is substantially parallel to the longitudinal axis.

In another embodiment, the fixation implant includes a button with a first button hole and a second button hole. The at least one strand of suture comprises a first strand of suture that passes through the first button hole and a suture construct that passes through both the first button hole and the second button hole. The suture construct includes a first free strand and a second free strand, and the suture construct includes a first adjustable eyesplice and a second adjustable eyesplice interconnected by a loop to form an adjustable loop.

In another embodiment, the first adjustable eyesplice of the suture construct is received in the first groove and the third groove of the graft preparation card, and the second adjustable eyesplice of the suture construct is received in the second groove and the fourth groove of the graft preparation card. The first adjustable eyesplice is slidable through the first slit to be received in the first hole, the second adjustable eyesplice is slidable through the second slit to be received in the second hole, and the loop of the suture construct is located between the first hole and the second hole.

In another embodiment, the first suture strand and the two free strands of the suture construct wrap around a first cleat and a second cleat of the graft preparation card.

In another embodiment, the tape suture assembly includes a second suture strand, the second suture strand extends from the distal end portion of the tape suture, and the tape suture is attached to the graft with the stitch formed by the second suture strand.

In another embodiment, the first suture strand and the second suture strand of the tape suture assembly form at least two v shaped stitches and at least two upside down v shaped stitches to secure the tape suture to the graft.

In another embodiment, a needle is attached to the first suture strand and the second suture strand.

In another embodiment, the first suture strand forms a stitch that passes through the graft and the tape suture of the tape suture assembly, loops over the proximal end of the graft and the proximal end of the tape suture to loop through the adjustable loop of the two adjustable eyesplices, and passes through the graft and the tape suture.

In another example, a method of preparing a graft includes inserting a graft preparation card into a slot of a tenaculum. A strand of suture of a fixation implant is wrapped around the graft preparation card. The method includes pivoting a first arm and a second arm of the tenaculum about a pivot such that a first tooth of the first arm pierces a proximal end portion of a tape suture of a tape suture assembly and a second tooth of the second arm pierces a proximal end portion of a graft. The method includes creating a stitch with a first suture strand of the tape suture assembly to secure the tape suture of the tape suture assembly to the graft.

In another embodiment, the tape suture assembly includes a second suture strand, and the step of creating the stitch includes creating a first stitch by passing a needle from a first side of the graft through the graft at a first location to position the needle on an opposite second side of the graft, spreading apart the first suture strand and the second suture strand to create an opening, moving the first suture strand and the second suture strand to the first side of the graft by passing the graft through the opening, and passing the needle from the first side of the graft through the tape suture and the graft at a second location proximal of the first location.

In another embodiment, the method includes the step of creating a second stitch by passing the needle, the first suture strand, and the second suture strand over the proximal end portion of the graft and the proximal end portion of the tape suture, passing the needle, the first suture strand, and the second suture strand through an adjustable loop of the fixation implant, and passing the needle, the first suture strand, and the second suture strand from the first side of the graft through the graft and the tape suture at a third location proximal of the second location.

In another embodiment, the method includes the step of preparing a graft including creating a third stitch by spreading apart the first suture strand and the second suture strand to create the opening, moving the first suture strand and the second suture strand to the first side of the graft by passing the graft through the opening, and passing the needle from the first side of the graft through the tape suture and the graft at the first location.

In another embodiment, the method includes the step of cutting one of the first suture strand and the second suture strand near the needle, tying a knot with the first suture strand and the second suture strand, piercing the needle in the graft to bury the knot in the graft, unwrapping the at least one strand of suture of the fixation implant from the graft fixation card, and removing the adjustable loop of the fixation implant from the graft fixation card.

BRIEF DESCRIPTION OF THE DRAWINGS

The various features and advantages will become apparent to those skilled in the art from the following detailed description of the currently preferred embodiment. The drawings that accompany the detailed description can be briefly described as follows:

FIGS. 9A to 9D illustrate forming a first stitch with sutures strands of the tape suture assembly in a proximal direction to secure the tape suture to the graft;

DETAILED DESCRIPTION

Figure 1:
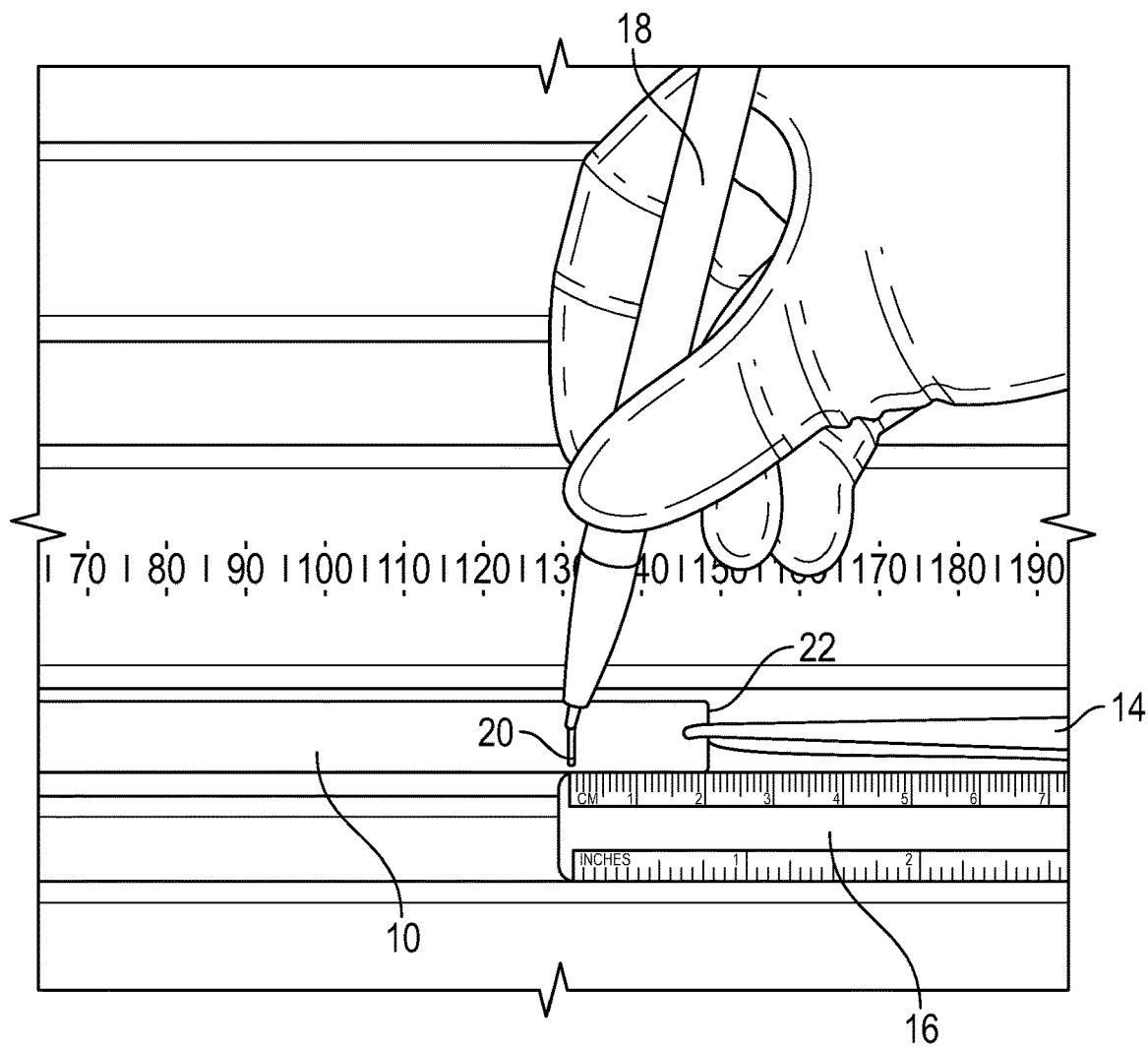
FIG. 1 illustrates the measuring of a graft.

Grafts are prepared prior to surgery to provide reinforcement. Sutures can be sewn into the graft with a needle to provide a scaffold to provide additional strength.

A graft preparation system includes a fixation implant including two strands of suture and a suture construct. The suture construct includes a first adjustable eyesplice and a second adjustable eyesplice interconnected by a loop to form an adjustable loop. The graft preparation system includes a graft preparation card, and the two strands of suture of the fixation implant are wrapped around the graft preparation card. The first arm includes a slot that receives the graft preparation card. The graft preparation system includes a tenaculum including a first arm having a first tooth and a second arm having a second tooth. The first tooth of the tenaculum pierces a tape suture, and the second tooth of the tenaculum pierces the graft. The graft preparation system includes a tape suture assembly including the tape suture, a first suture strand, and a second suture strand. The tape suture is attached to the graft with stitches formed with the first suture strand and the second suture strand. The fixation implant is attached to the graft with a stitch formed with the first suture strand and the second suture strand that passes through the adjustable loop.

In one example, a graft preparation system includes a fixation implant including a button with a first button hole and a second button hole, a first strand of suture that passes through the first button hole, and a suture construct that passes through both the first button hole and the second button hole. The suture construct includes a first free strand and a second free strand, and the suture construct includes a first adjustable eyesplice and a second adjustable eyesplice interconnected by a loop to form an adjustable loop. The graft preparation system includes a graft preparation card substantially rectangular in shape and including a graft edge, an opposing tenaculum edge, a first cleat edge that defines a first cleat, and an opposing second cleat edge that defines a second cleat. The graft preparation card includes a passage having a longitudinal axis extending from the graft edge, a first hole and a second hole located on each side of the passage, a first slit that extends from the graft edge to the first hole, and a second slit that extends from the graft edge to the second hole. The graft preparation card includes a first groove on the graft edge located above the first hole, a second groove on the graft edge located above the second hole, a third groove located on the tenaculum edge, and a fourth groove is located on the tenaculum edge. A line extending between the first groove and the third groove is substantially parallel to the longitudinal axis and a line between the second groove and the fourth groove is substantially parallel to the longitudinal axis. The first strand of suture, the first free strand, and the second free strand of the fixation implant are wrapped around the graft preparation card. The first adjustable eyesplice of the suture construct is received in the first groove and the third groove of the graft preparation card, and the second adjustable eyesplice of the suture construct is received in the second groove and the fourth groove of the graft preparation card. The first adjustable eyesplice is slidable through the first slit to be received in the first hole, and the second adjustable eyesplice is slidable through the second slit to be received in the second hole. The loop of the suture construct is located between the first hole and the second hole. The graft preparation system includes a tenaculum including a first arm having a first tooth and a second arm having a second tooth. The first arm and the second arm are pivotally connected at a pivot, and the first tooth and the second tooth are at a distal end of the first arm and the second arm, respectively, of the tenaculum. The first arm between the first tooth and the pivot includes a slot that receives the graft preparation card. The graft preparation system includes a tape suture assembly including a tape suture, a first suture strand, a second suture strand, and a needle attached to the first suture strand and the second suture strand. The tape suture is positioned on a graft, the first suture strand and the second suture strand extend from a distal end portion of the tape suture, and the tape suture is attached to the graft with stitches formed by the first suture strand and the second suture strand. The first tooth of the tenaculum pierces a proximal end portion of the tape suture, the second tooth of the tenaculum pierces a proximal end portion of the graft, and the first suture strand and the two free strands of the suture construct wrap around a first cleat and a second cleat of the graft preparation card.

In another example, a graft preparation system includes a fixation implant including at least one strand of suture and a graft preparation card. The at least one strand of suture of the fixation implant is wrapped around the graft preparation card. The graft preparation system includes a tenaculum including a first arm having a first tooth and a second arm having a second tooth, and the first arm and the second arm are pivotally connected at a pivot. The first arm between the first tooth and the pivot includes a slot that receives the graft preparation card. The graft preparation system includes a tape suture assembly including a tape suture and a first suture strand. The tape suture is positioned on a graft, and the first suture strand extends from a distal end portion of the tape suture. The tape suture is attached to the graft with a stitch formed with the first suture strand, the first tooth of the tenaculum pierces a proximal end portion of the tape suture, and the second tooth of the tenaculum pierces a proximal end portion of the graft.

In another example, a method of preparing a graft includes inserting a graft preparation card into a slot of a tenaculum. A strand of suture of a fixation implant is wrapped around the graft preparation card. The method includes pivoting a first arm and a second arm of the tenaculum about a pivot such that a first tooth of the first arm pierces a proximal end portion of a tape suture of a tape suture assembly and a second tooth of the second arm pierces a proximal end portion of a graft. The method includes creating a stitch with a first suture strand of the tape suture assembly to secure the tape suture of the tape suture assembly to the graft.

FIG. 1 illustrates a graft 10 of a graft preparation system. A proximal end region 12 of the graft 10 is held by an instrument 14. A ruler 16 is positioned next to the graft 10 and is used to locate a desired location on the graft 10 based on a desired length of stitches. The graft 10 is marked at the desired location with a marker 18 to form a line 20. In one example, the desired location is approximately 2.0 cm from the proximal edge 22 of the graft 10. In one example, the graft 10 is a quad tendon graft.

Figure 2:
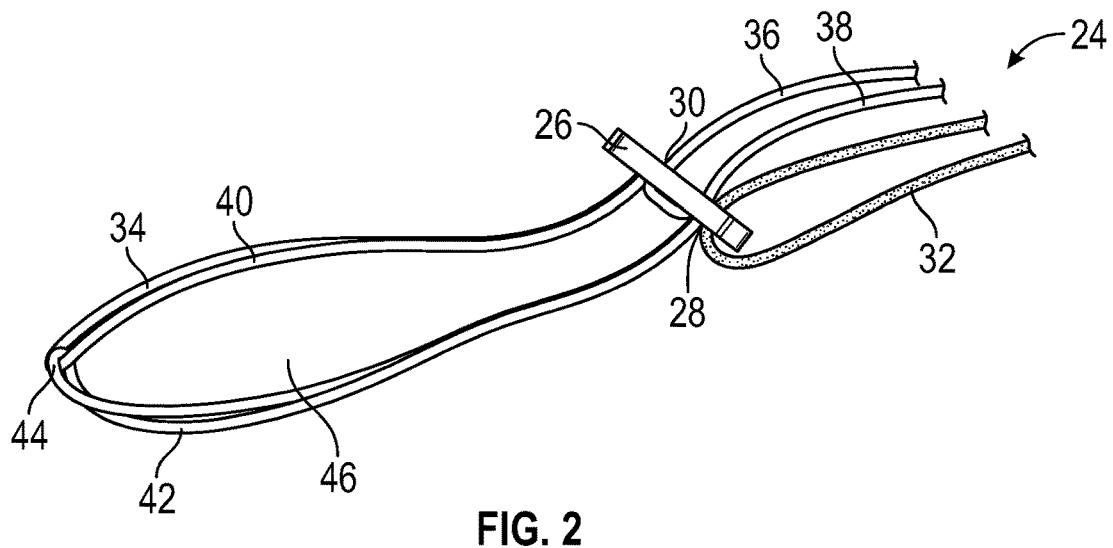
FIG. 2 illustrates a fixation implant.

FIG. 2 illustrates a fixation implant 24. In one example, the fixation implant 24 is a TightRope® fixation implant 24 manufactured by Arthrex, Inc. of Naples, Fla. The fixation implant 24 includes a button 26 including a first hole 28 and a second hole 30. A suture strand 32 passes through the first hole 28. A suture construct 34 passes though both the first hole 28 and the second hole 30. The suture construct 34 includes two free strands 36 and 38 and two adjustable eyesplices 40 and 42 that are interconnected at a loop 44 to form an adjustable loop 46. The button 26 provides cortical bone fixation of the graft 10. The loop 46 has an adjustable length and is connected to or supports the graft 10. By pulling on the free strands 36 and 38, the individual eyesplices 40 and 42, respectively, constrict and reduce the size of the loop 46. A force can be also be applied interior to one or both of the eyesplices 40 and 42 to elongate the individual eyesplices 40 and 42.

Figure 3:
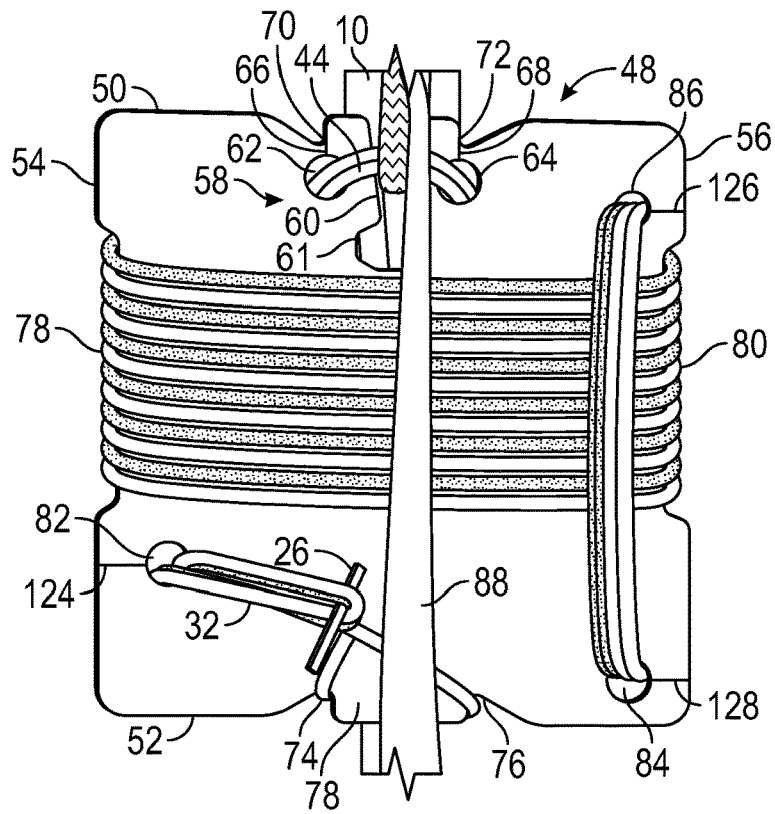
FIG. 3 illustrates a front side of a graft preparation card with suture strands of the fixation implant wrapped around the graft preparation card.
Figure 4:
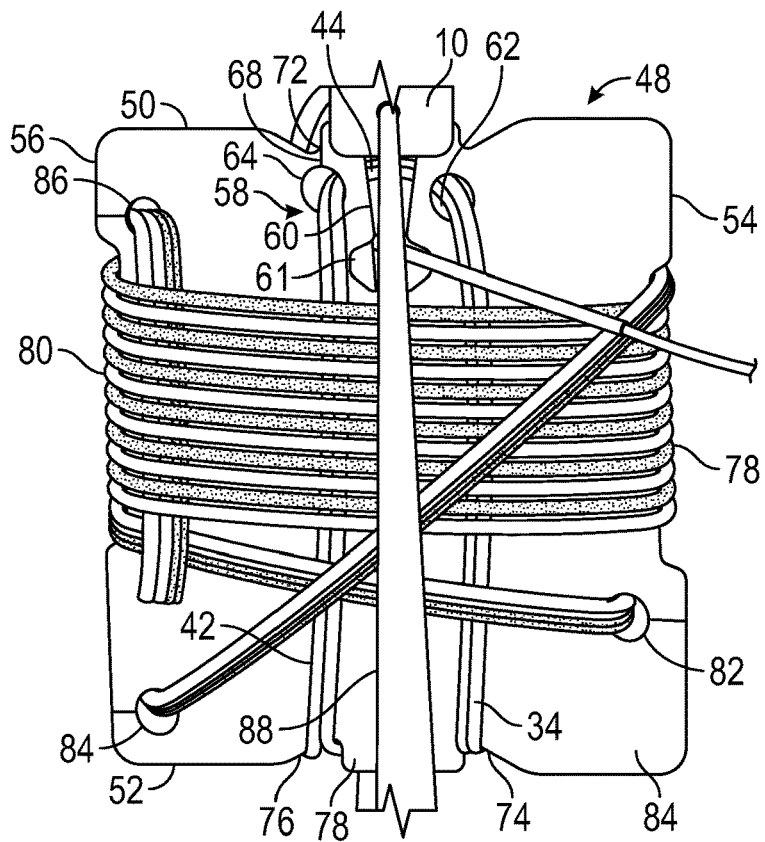
FIG. 4 illustrates a back side of the graft preparation card with the suture strands of the fixation implant wrapped around the graft preparation card.

FIGS. 3 and 4 illustrate a graft preparation card 48. The graft preparation card 48 is substantially rectangular in shape and includes a graft edge 50, an opposing tenaculum edge 52, a first cleat edge 54, and an opposing second cleat edge 56. The graft preparation card 48 includes a keyhole shaped opening 58 extending from the graft edge 50. The keyhole shaped opening 58 has a longitudinal axis A. The keyhole shaped opening 58 includes a passage 60 extending inwardly from the graft edge 50 and a curved portion 61 in communication with the passage 60. In one example, the curved portion 61 is oval.

A hole 62 and 64 is located on each side of the passage 60 of the keyhole shaped opening 58. A slit 66 and 68 extends from the graft edge 50 to each of the holes 62 and 64, respectively. A groove 70 and 72 is located above each hole 62 and 64, respectively, on the graft edge 50. The tenaculum edge 52 includes two grooves 74 and 76 each aligned with one of the grooves 70 and 72, respectively, of the graft edge 50. A tab 78 is defined between the two grooves 74 and 76.

The first cleat edge 54 and the opposing second cleat edge 54 each define a cleat 78 and 80, respectively. A first hole 82 is located in an area where the tenaculum edge 52 and the first cleat edge 54 meet, a second hole 84 is located in an area where the tenaculum edge 52 and the opposing second cleat edge 54 meet, and a third hole 86 is located in an area where the graft edge 50 and the opposing second cleat edge 54 meet. A slit 124, 126, and 128 extends from the closest cleat edge 54 and 56 to each of the holes 82, 84, and 86, respectively. A line defined between the second hole 84 and the third hole 86 is substantially parallel to the longitudinal axis A.

The button 26 is located on the front side of the graft preparation card 48. The eyesplices 40 and 42 of the suture construct 34 extend from the button 26 and are each received in one of the grooves 74 and 76, respectively, on the tenaculum edge 52 of the graft preparation card 48. The eyesplices 40 and 42 extend on the back side of the graft preparation card 48 such that the eyesplices 40 and 42 are received in the grooves 70 and 72 on the graft edge 50. The eyesplices 40 and 42 of the suture construct 34 are each slid through one of the slits 66 and 68, respectively, to be received in the holes 62 and 64, respectively, and the loop 44 of the suture construct 34 is located between the holes 62 and 64.

The suture strand 32 and the free ends 36 and 38 of the suture construct 34 pass through the slit 124 and into the first hole 82 and are wrapped several times around the graft preparation card 48 such that the suture strand 32 and the free ends 36 and 38 of the suture construct 34 are received over the cleats 78 and 80. The suture strand 32 and the free ends 36 and 38 of the suture construct 34 then extend from the cleat 78 on the first cleat edge 54 of the graft preparation card 48 diagonally across the back side of the graft preparation card 48 over the wrapped sutures and pass through the slit 128 and into the second hole 84. The suture strand 32 and the free ends 36 and 38 of the suture construct 34 extend substantially parallel to the longitudinal axis A on the front side of the graft preparation card 48 and pass through the slit 126 and into the third hole 86. Ends of suture strand 32 and the free ends 36 and 38 of the suture construct 34 are then secured under other sutures.

Figure 5:
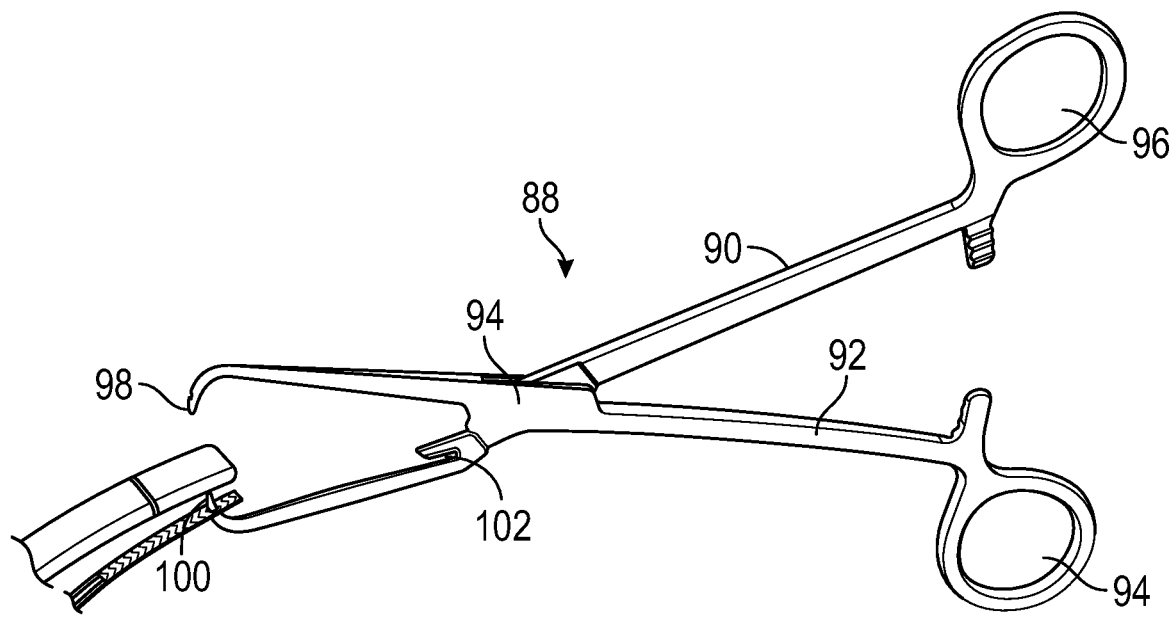
FIG. 5 illustrates a tenaculum.

FIG. 5 illustrates an instrument that retains the graft preparation card 48. In one example, the instrument is a tenaculum 88 including two arms 90 and 92 connected at a pivot 94. One end of each arm 90 and 92 includes a finger receiving hole 94 and 96, respectively, and the opposing end of each arm 90 and 92 includes a tooth 98 and 100, respectively. In one example, each tooth 98 and 100 defines a point. The arm 92 includes a slot 102 near the pivot 94 on a portion of the arm 92 located between the pivot 94 and the tooth 100. The slot 102 receives the graft preparation card 48.

Figure 6:
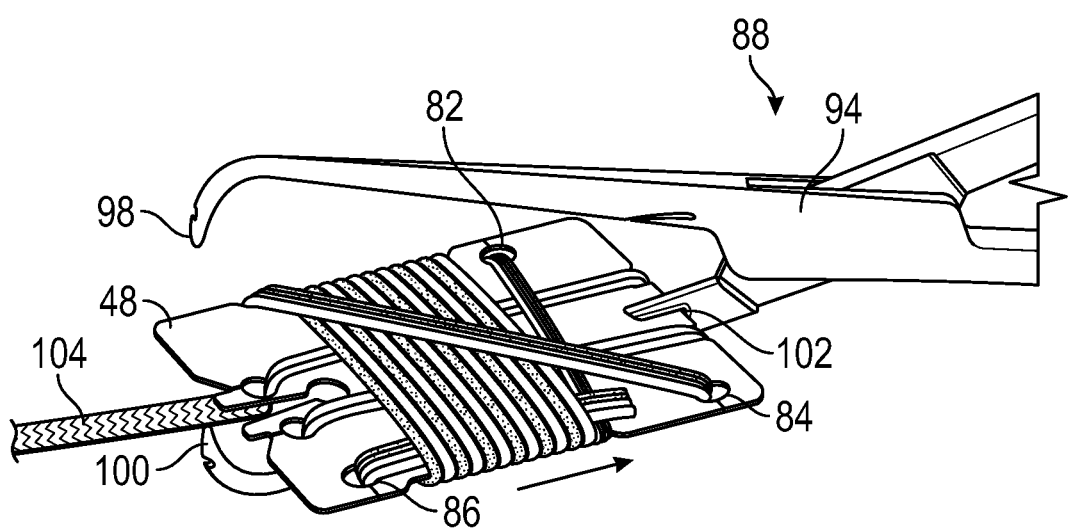
FIG. 6 illustrates the graft preparation card received in a slot of the tenaculum.

The graft preparation card 48 is removed from a larger packaging card 48 (not shown). As shown in FIG. 6, the tab 78 on the opposing tenaculum edge 52 of the graft preparation card 48 is positioned in the slot 102 of the tenaculum 88. An end region of a tape suture 104 of a tape suture assembly 105 is positioned to be is proximate to the tooth 100 of the tenaculum 88. The tape suture assembly 105 includes the tape suture 104, two free strands of suture 106 and 108 attached to an opposing end region of the tape suture 104 (shown in FIG. 7), and a needle 110 (shown in FIGS. 9A to 9C). In one example, the tape suture is a FiberTag® suture manufactured by Arthrex, Inc. of Naples, Fla.

Figure 7:
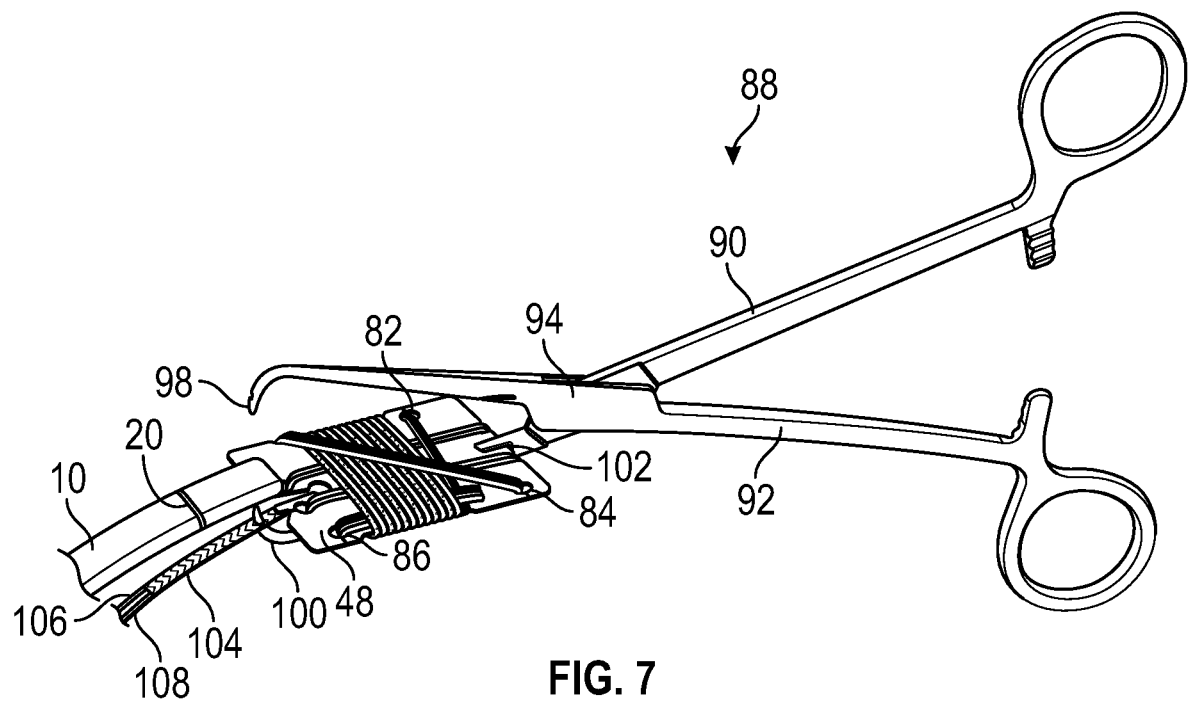
FIG. 7 illustrates a tooth of the tenaculum piercing a tape suture of a tape suture assembly.

As shown in FIG. 7, the arms 90 and 92 of the tenaculum 88 are then brought together such that the tooth 100 of one arm 90 of the tenaculum 88 pierces the tape suture 104. The fixation implant 24 is not pierced by the teeth 98 and 100 of the tenaculum 88.

Figure 8:
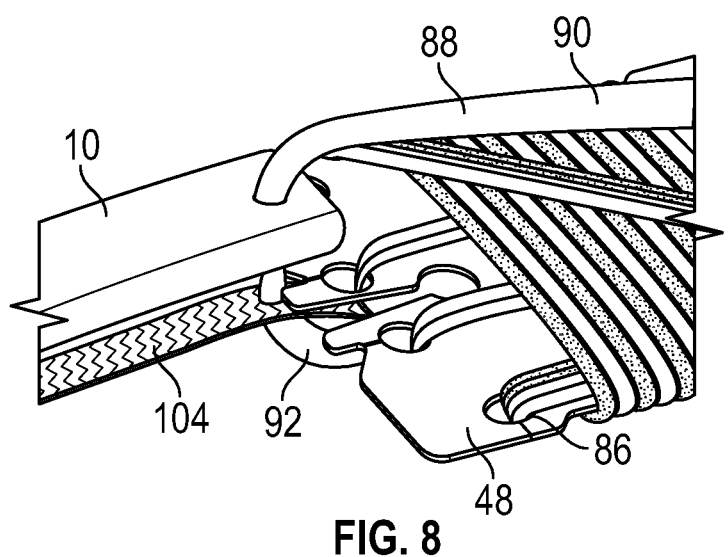
FIG. 8 illustrates another tooth of the tenaculum piercing a graft.

As shown in FIG. 8, the tooth 98 of the other arm 92 of the tenaculum 88 pierces the proximal edge 22 of the graft 10. In one example, the tenaculum 88 is clamped approximately 2 mm from the proximal edge 22 of the graft 10.

Figure 9C:
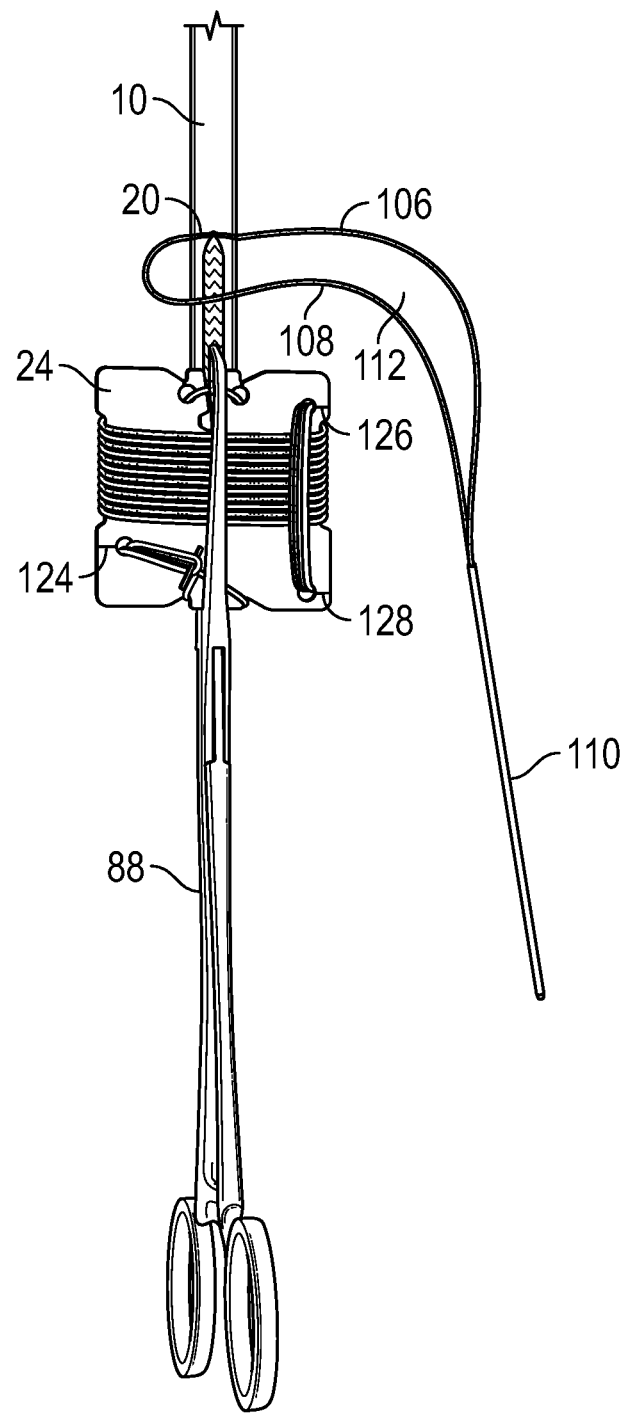
Figure 9D:
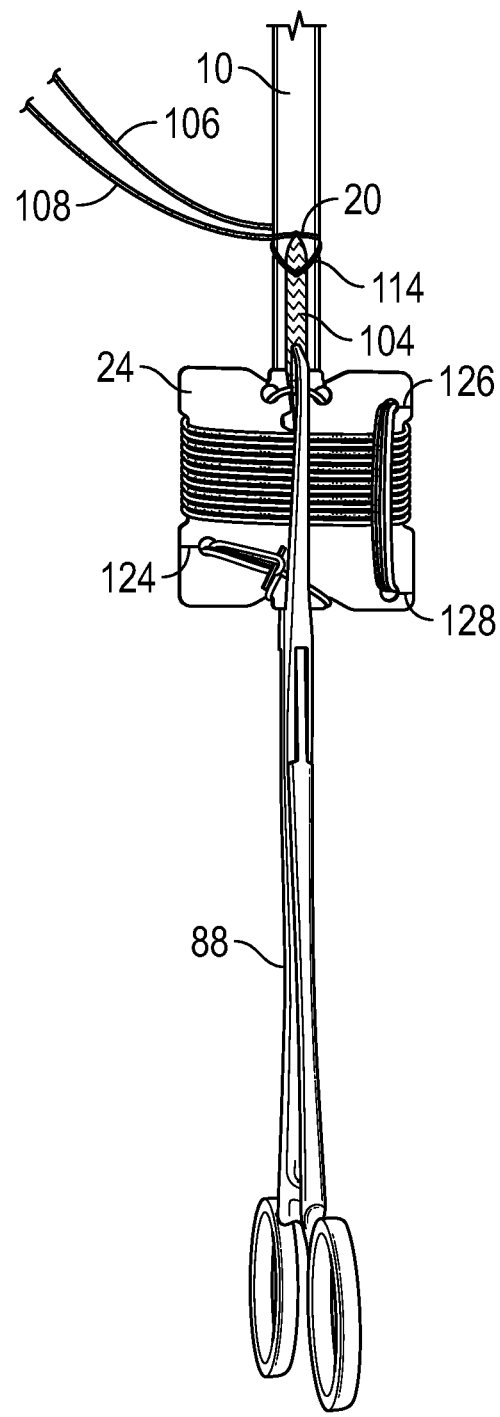

As shown in FIGS. 9A to 9D, the tape suture 104 is then attached to the graft 10 using the two free strands of suture 106 and 108 of the tape suture assembly 105. As shown in FIG. 9A, the length and position of the tape suture 104 is determined using an initial pass of the needle 110 through the graft 10 at the line 20 drawn by the marker 18. As shown in FIG. 9B, the needle 110 has passed through the graft 10 such that the needle 110 is located on the back side of the graft 10. The two free strands of suture 106 and 108 are then spread apart to create an opening 112, and the two free strands of suture 106 and 108 and the needle 110 are moved to the front side of the graft 10 by passing the graft 10 through the opening 112. As shown in FIG. 9D, the needle 110 is then positioned proximally and passes through the tape suture 104 and the graft 10 to be positioned on the back side of the graft 10, capturing the tape suture 104 by creating a first stitch 114. Moving proximally, a second stitch 116 is created repeating these steps. Additional stitches can be created in the same manner if needed. In the example shown, two stitches 114 and 116 are formed.

Figure 10A:
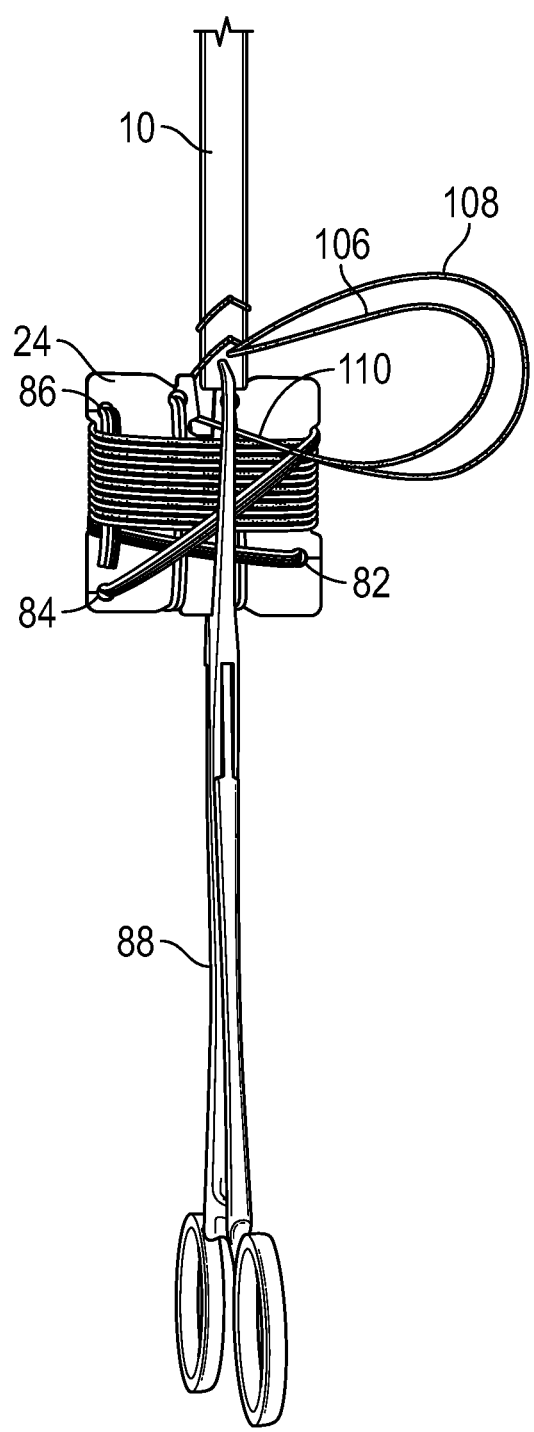
FIGS. 10A to 10D illustrate the formation of stitches with the sutures strands of the tape suture assembly to secure the tape suture to the graft.

As shown in FIG. 10A, the needle 110 is located on the back side of the graft 10. The two free strands of suture 106 and 108 pass through the passage 60 in the keyhole shaped opening 58 of the graft preparation card 48 to capture and loop through the two adjustable eyesplices 40 and 42 of the fixation implant 24. The needle 110 then passes through the tape suture 104 and the graft 10 at a location proximal to the two stitches 114 and 116 to create a third stitch 117. The needle 110 is located on the back side of the graft 10. The fixation implant 24 is then secured to the graft 10.

Figure 10B:
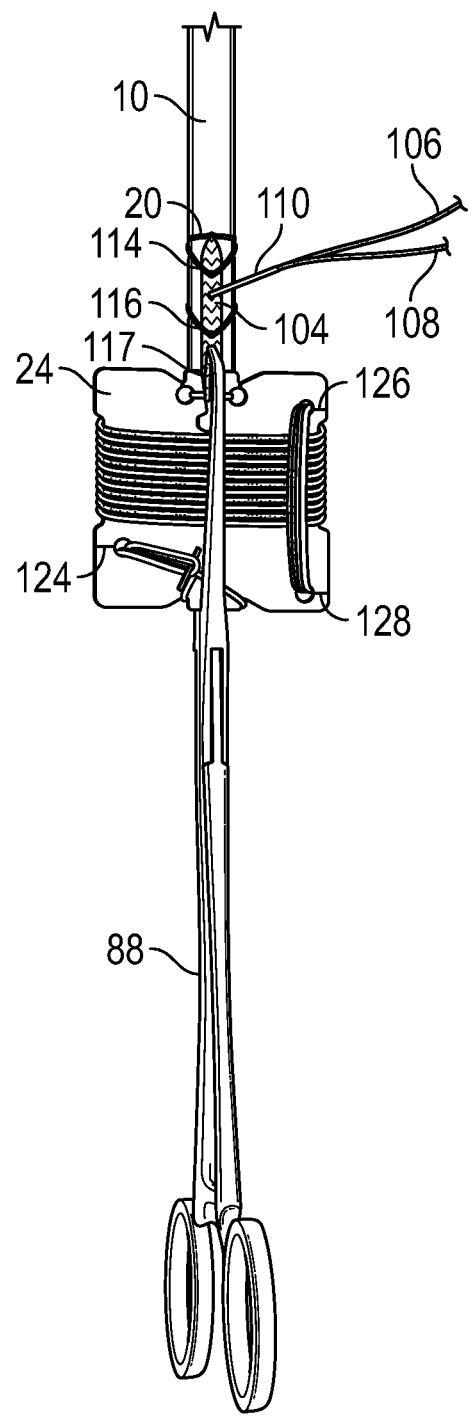

The two free strands of suture 106 and 108 are then spread apart to create an opening 112, and the two free strands of suture 106 and 108 and the needle 110 are then moved to the front side of the graft 10 by passing the graft 10 through the opening 112. As shown in FIG. 10B, the needle 110 with the two free strands of suture 106 and 108 passes through the graft 10 and the tape suture 104 from the front side at a location between the first stitch 114 and the second stitch 116, creating a fourth stitch 118. The needle 110 is then located at the back side of the graft 10.

The two free strands of suture 106 and 108 are spread apart to create an opening 112, and the two free strands of suture 106 and 108 and the needle 110 are then moved to the front side of the graft 10, capturing the tape suture 104 with a fourth stitch 118. Moving distally, a fifth stitch 120 is created repeating these steps. Additional stitches can be created in the same manner if needed. In the example shown, two stitches 118 and 120 are formed.

Figure 10C:
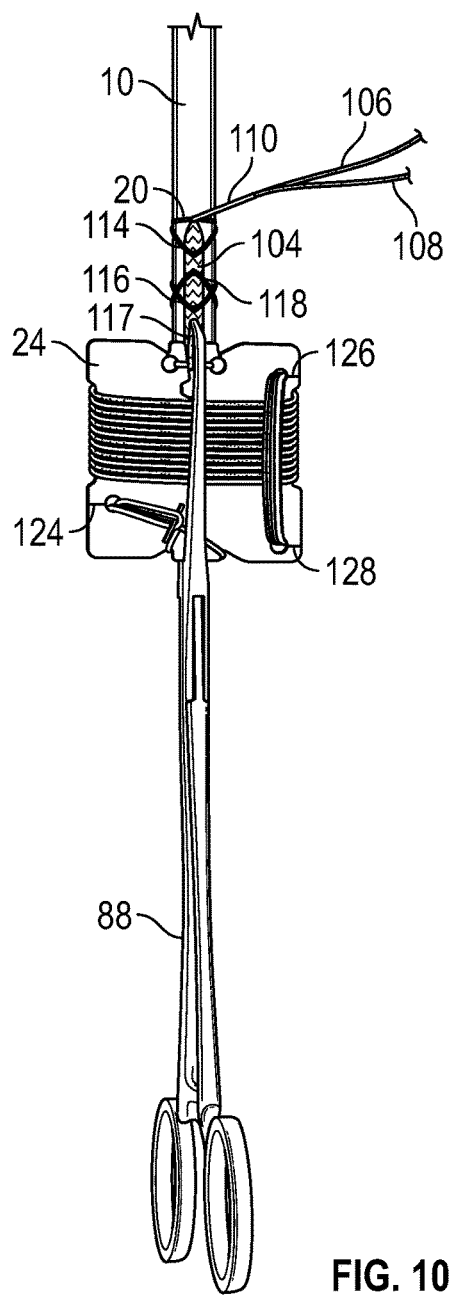
Figure 10D:
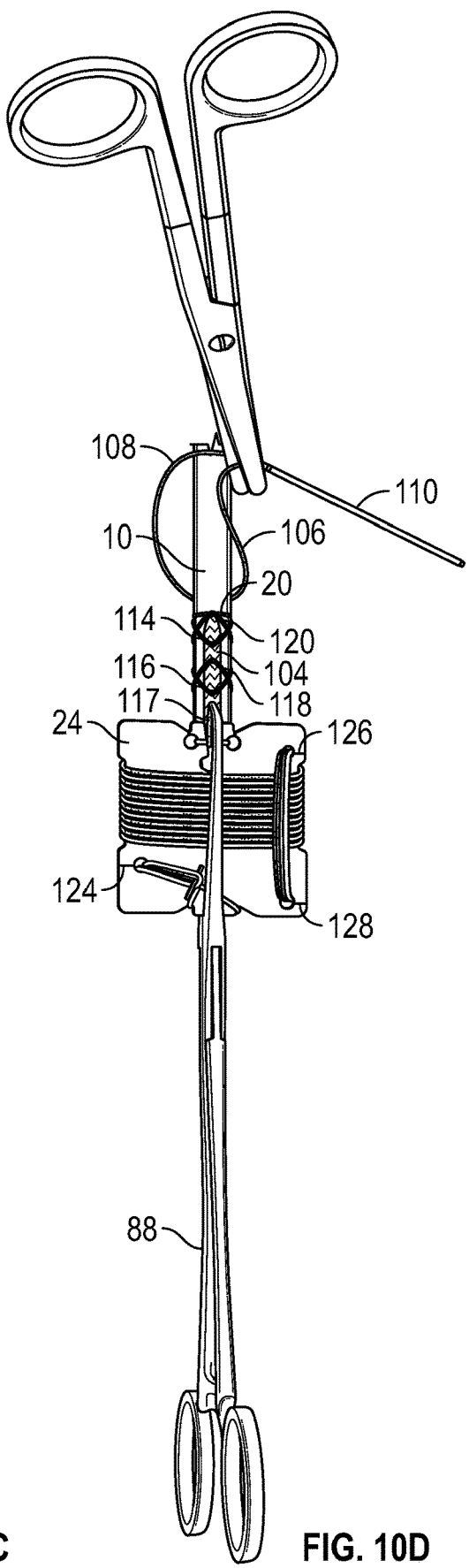

As shown in FIG. 10C, the needle 110 completes the fifth stitch 120 at the end of the tape suture 104 at the line 20 to assist with burying a knot 122 (shown in FIG. 11A), which is later tied. As shown in FIG. 10D, one of the two free strands of suture 106 is cut right below the needle 110.

Figure 11A:
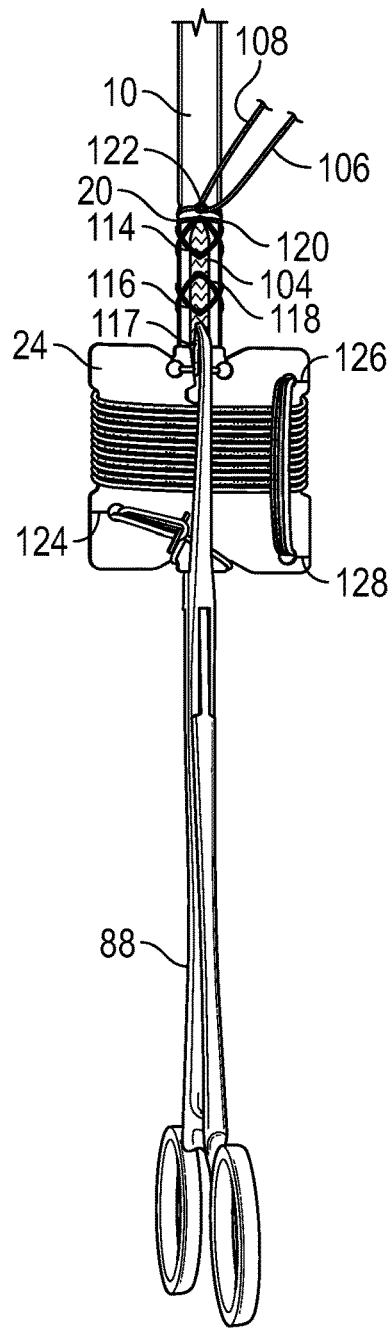
FIGS. 11A to 11D illustrate the formation of a knot with the sutures strands of the tape suture assembly.
Figure 11B:
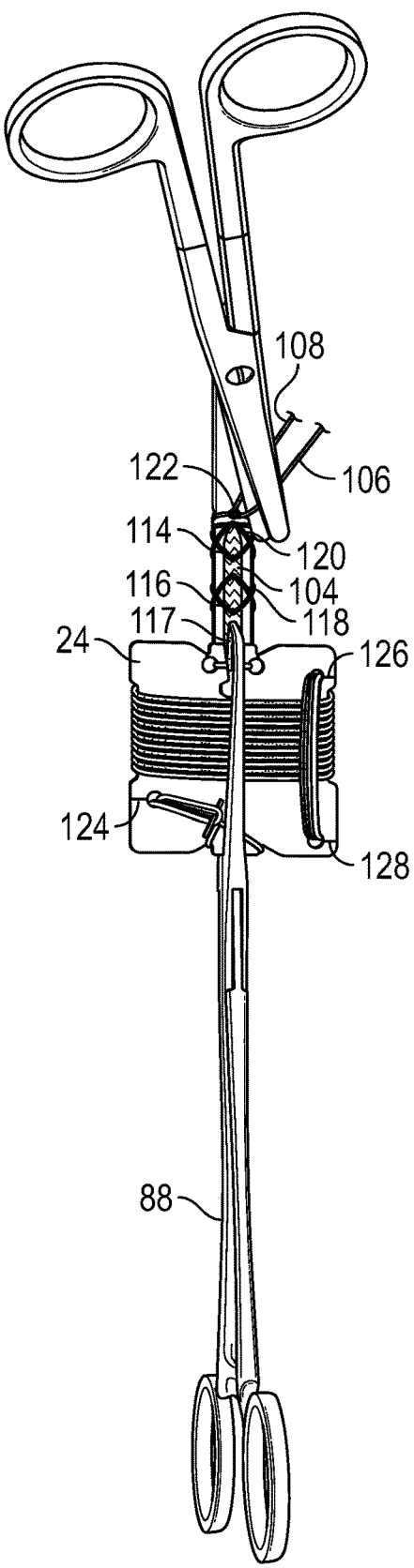
Figure 11C:
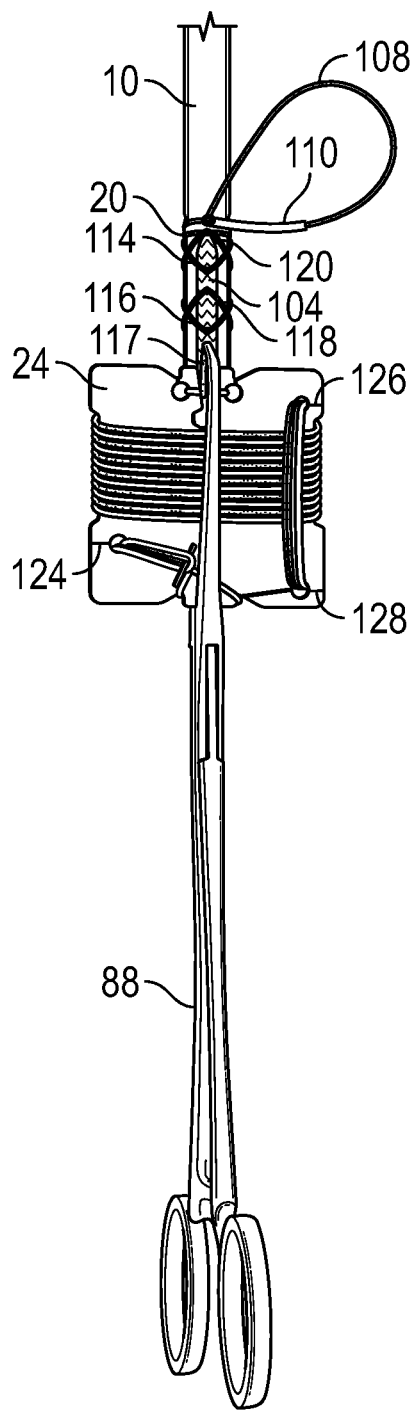
Figure 11D:
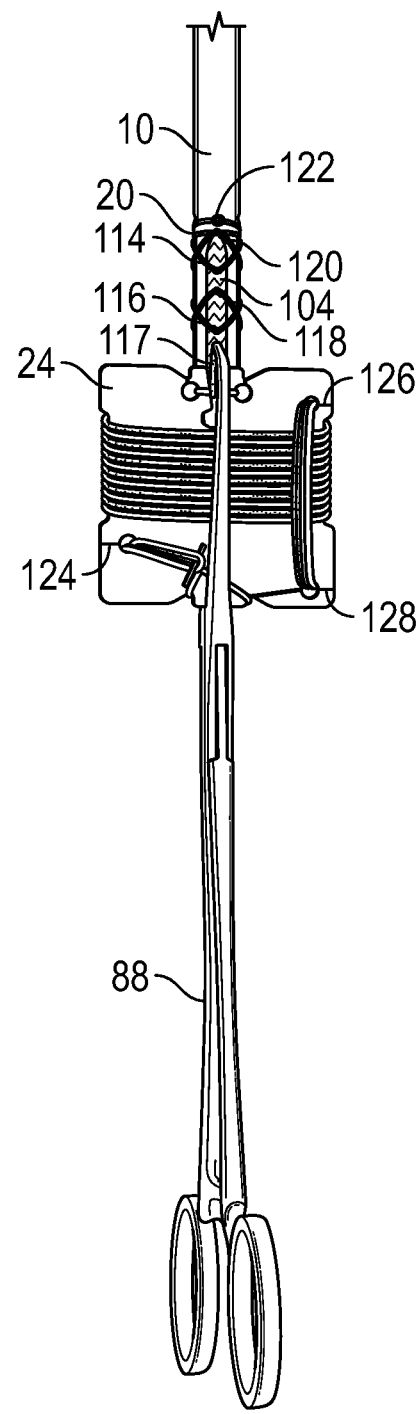
Figure 12:
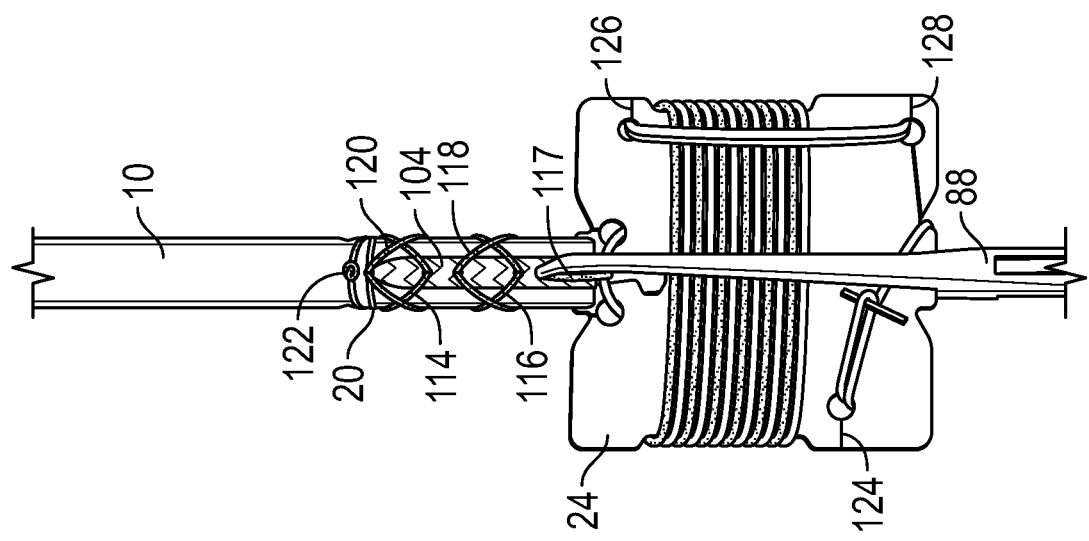
FIG. 12 illustrate the front side of the graft preparation card and the fixation implant attached to the graft after cutting the suture strands of the tape suture assembly.

As shown in FIG. 11A, the two free strands of suture 106 and 108 are wrapped around the graft 10 in a cerclage manner, and a knot 122 is tied to secure the construct. As shown in FIG. 11B, the free suture strand 106 without the needle 110 is cut just above the knot 122. As shown in FIG. 11C, the needle 110 is pierced through the graft 10 and the knot 122 to pull the knot 112 through the graft 10. Tension is applied to the free suture strand 108 to bury the knot 122 in the graft 10. As shown in FIGS. 11D and 12, the free suture strand 108 with the needle 110 is cut flush to the graft 10.

Figure 13:
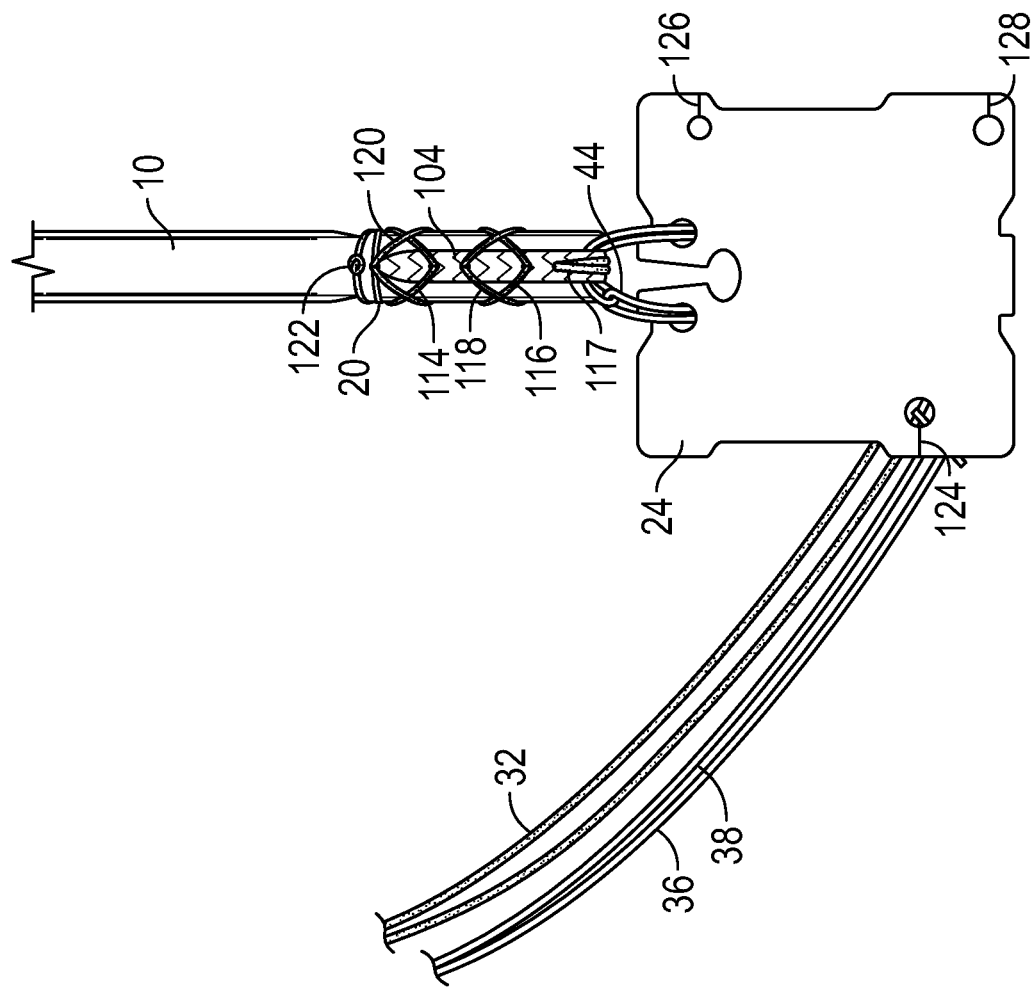
FIG. 13 illustrates the front side of the graft preparation card and the fixation implant attached to the graft after the suture strands of the fixation implant are unwrapped from the graft preparation card.
Figure 14:
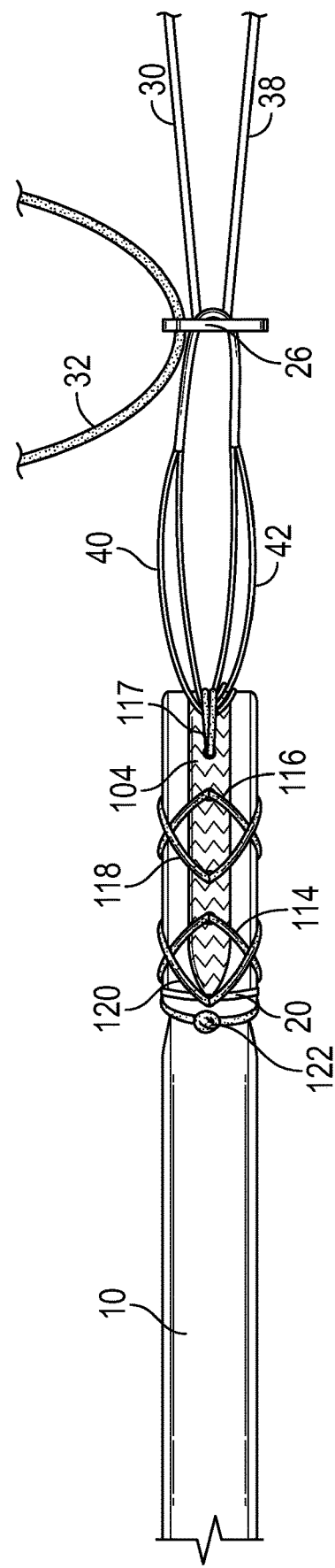
FIG. 14 illustrates the fixation implant attached to the prepared graft.

As show in FIG. 13, the tenaculum 88 can be removed from the graft preparation card 48. The suture strand 32 and the two free strands 36 and 38 of the fixation implant 24 are unwrapped from the graft preparation card 48. The two adjustable eyesplices 40 and 42 are removed from the slits 66 and 68 in the graft preparation card 48. FIG. 14 show the graft 10 in a final prepared state, with the fixation implant 24 attached and ready to be used in a surgical procedure.

It should be understood that many additional changes in the details, materials, steps and arrangements of parts, which have been herein described and illustrated in order to explain the nature of the present embodiments, may be made by those skilled in the art while still remaining within the principles and scope of the disclosed embodiments.

What is claimed is:

1. A graft preparation system comprising:
    a fixation implant including a button with a first button hole and a second button hole, a first strand of suture that passes through the first button hole, and a suture construct that passes through both the first button hole and the second button hole, wherein the suture construct includes a first free strand and a second free strand, and the suture construct includes a first adjustable eyesplice and a second adjustable eyesplice interconnected by a loop to form an adjustable loop;
    a graft preparation card substantially rectangular in shape and including a graft edge, an opposing tenaculum edge, a first cleat edge that defines a first cleat, an opposing second cleat edge that defines a second cleat, a passage having a longitudinal axis extending from the graft edge, a first hole and a second hole located on each side of the passage, a first slit that extends from the graft edge to the first hole, a second slit that extends from the graft edge to the second hole, a first groove on the graft edge located above the first hole, a second groove on the graft edge located above the second hole, a third groove located on the tenaculum edge, and a fourth groove is located on the tenaculum edge,
        wherein a line extending between the first groove and the third groove is substantially parallel to the longitudinal axis and a line between the second groove and the fourth groove is substantially parallel to the longitudinal axis,
        wherein the first strand of suture, the first free strand, and the second free strand of the fixation implant are wrapped around the graft preparation card,
        wherein the first adjustable eyesplice of the suture construct is received in the first groove and the third groove of the graft preparation card and the second adjustable eyesplice of the suture construct is received in the second groove and the fourth groove of the graft preparation card,
        wherein the first adjustable eyesplice is slidable through the first slit to be received in the first hole and the second adjustable eyesplice is slidable through the second slit to be received in the second hole, and
        wherein the loop of the suture construct is located between the first hole and the second hole;
    a tenaculum including a first arm having a first tooth and a second arm having a second tooth, wherein the first arm and the second arm are pivotally connected at a pivot, the first tooth and the second tooth are at a distal end of the first arm and the second arm, respectively, of the tenaculum, and the first arm between the first tooth and the pivot includes a slot that receives the graft preparation card; and
    a tape suture assembly including a tape suture, a first suture strand, a second suture strand, and a needle attached to the first suture strand and the second suture strand, wherein the tape suture is positioned on a graft, the first suture strand and the second suture strand extend from a distal end portion of the tape suture, the tape suture is attached to the graft with stitches formed by the first suture strand and the second suture strand, the first tooth of the tenaculum pierces a proximal end portion of the tape suture, the second tooth of the tenaculum pierces a proximal end portion of the graft, and the first suture strand and the two free strands of the suture construct wrap around a first cleat and a second cleat of the graft preparation card.

2. A graft preparation system comprising:
    a fixation implant including at least one strand of suture;
    a graft preparation card, wherein the at least one strand of suture of the fixation implant is wrapped around the graft preparation card;
    a tenaculum including a first arm having a first tooth and a second arm having a second tooth, wherein the first arm and the second arm are pivotally connected at a pivot, and the first arm between the first tooth and the pivot includes a slot that receives the graft preparation card; and a tape suture assembly including a tape suture and a first suture strand, wherein the tape suture is positioned on a graft, the first suture strand extends from a distal end portion of the tape suture, the tape suture is attached to the graft with a stitch formed with the first suture strand, the first tooth of the tenaculum pierces a proximal end portion of the tape suture, and the second tooth of the tenaculum pierces a proximal end portion of the graft.

3. The graft preparation system as recited in claim 2, wherein the first tooth and the second tooth are at a distal end of the first arm and the second arm, respectively, of the tenaculum.

4. The graft preparation system as recited in claim 2, wherein the graft preparation card is substantially rectangular in shape and includes a graft edge, an opposing tenaculum edge, a first cleat edge, and an opposing second cleat edge, and the graft preparation card includes a passage having a longitudinal axis extending from the graft edge.

5. The graft preparation system as recited in claim 4, wherein the graft preparation card includes a curved portion in communication with the passage, and the passage and the curved portion define a keyhole shaped opening.

6. The graft preparation system as recited in claim 4, wherein the graft preparation card includes a first hole and a second hole located on each side of the passage, a first slit extends from the graft edge to the first hole, and a second slit extends from the graft edge to the second hole.

7. The graft preparation system as recited in claim 6, wherein a first groove on the graft edge is located above the first hole, a second groove on the graft edge is located above the second hole, a third groove is located on the tenaculum edge, a fourth groove is located on the tenaculum edge, wherein a line extending between the first groove and the third groove is substantially parallel to the longitudinal axis, and a line between the second groove and the fourth groove is substantially parallel to the longitudinal axis.

8. The graft preparation system as recited in claim 7, wherein the first cleat edge defines a first cleat, the opposing second cleat edge defines a second cleat, a third hole is located in an area where the tenaculum edge and the first cleat edge intersect, a fourth hole is located in an area where the tenaculum edge and the opposing second cleat edge intersect, and a fifth hole is located in an area where the graft edge and the opposing second cleat edge intersect, and a line between the fourth hole and the fifth hole is substantially parallel to the longitudinal axis.

9. The graft preparation system as recited in claim 8, wherein the fixation implant includes a button with a first button hole and a second button hole, the at least one strand of suture comprises a first strand of suture that passes through the first button hole and a suture construct that passes through both the first button hole and the second button hole, the suture construct includes a first free strand and a second free strand, and the suture construct includes a first adjustable eyesplice and a second adjustable eyesplice interconnected by a loop to form an adjustable loop.

10. The graft preparation system as recited in claim 9, wherein the first adjustable eyesplice of the suture construct is received in the first groove and the third groove of the graft preparation card, the second adjustable eyesplice of the suture construct is received in the second groove and the fourth groove of the graft preparation card, the first adjustable eyesplice is slidable through the first slit to be received in the first hole, the second adjustable eyesplice is slidable through the second slit to be received in the second hole, and the loop of the suture construct is located between the first hole and the second hole.

11. The graft preparation system as recited in claim 2, wherein the first suture strand and the two free strands of the suture construct wrap around a first cleat and a second cleat of the graft preparation card.

12. The graft preparation system as recited in claim 2, wherein the tape suture assembly includes a second suture strand, the second suture strand extends from the distal end portion of the tape suture, and the tape suture is attached to the graft with the stitch formed by the second suture strand.

13. The graft preparation system as recited in claim 12, wherein the first suture strand and the second suture strand of the tape suture assembly form at least two v shaped stitches and at least two upside down v shaped stitches to secure the tape suture to the graft.

14. The graft preparation system as recited in claim 2, including a needle attached to the first suture strand and the second suture strand.

15. The graft preparation system as recited in claim 2, wherein the first suture strand forms a stitch that passes through the graft and the tape suture of the tape suture assembly, loops over the proximal end of the graft and the proximal end of the tape suture to loop through the adjustable loop of the two adjustable eyesplices, and that passes through the graft and the tape suture.

16. A method of preparing a graft comprising:
inserting a graft preparation card into a slot of a tenaculum, wherein at least one strand of suture of a fixation implant is wrapped around the graft preparation card;
pivoting a first arm and a second arm of the tenaculum about a pivot such that a first tooth of the first arm pierces a proximal end portion of a tape suture of a tape suture assembly and a second tooth of the second arm pierces a proximal end portion of a graft; and
creating a stitch with a first suture strand of the tape suture assembly to secure the tape suture of the tape suture assembly to the graft.

17. The method of preparing a graft as recited in claim 16, wherein the tape suture assembly includes a second suture strand, and the step of creating the stitch includes creating a first stitch by passing a needle from a first side of the graft through the graft at a first location to position the needle on an opposite second side of the graft, spreading apart the first suture strand and the second suture strand to create an opening, moving the first suture strand and the second suture strand to the first side of the graft by passing the graft through the opening, and passing the needle from the first side of the graft through the tape suture and the graft at a second location proximal of the first location.

18. The method of preparing a graft as recited in claim 17, including creating a second stitch by passing the needle, the first suture strand, and the second suture strand over the proximal end portion of the graft and the proximal end portion of the tape suture, passing the needle, the first suture strand, and the second suture strand through an adjustable loop of the fixation implant, and passing the needle, the first suture strand, and the second suture strand from the first side of the graft through the graft and the tape suture at a third location proximal of the second location.

19. The method of preparing a graft as recited in claim 18, including creating a third stitch by spreading apart the first suture strand and the second suture strand to create the opening, moving the first suture strand and the second suture strand to the first side of the graft by passing the graft through the opening, and passing the needle from the first side of the graft through the tape suture and the graft at the first location.

20. The method of preparing a graft as recited in claim 19, including cutting one of the first suture strand and the second suture strand near the needle, tying a knot with the first suture strand and the second suture strand, piercing the needle in the graft to bury the knot in the graft, and unwrapping the at least one strand of suture of the fixation implant from the graft fixation card and removing the adjustable loop of the fixation implant from the graft fixation card.

* * * * *